United States Patent
Miyachi

(10) Patent No.: US 9,993,227 B2
(45) Date of Patent: Jun. 12, 2018

(54) ULTRASOUND DIAGNOSIS DEVICE AND ULTRASOUND IMAGE GENERATION METHOD

(71) Applicant: FUJIFILM Corporation, Tokyo (JP)

(72) Inventor: Yukiya Miyachi, Ashigara-kami-gun (JP)

(73) Assignee: FUJIFILM Corporation, Tokyo (JP)

( * ) Notice: Subject to any disclaimer, the term of this patent is extended or adjusted under 35 U.S.C. 154(b) by 208 days.

(21) Appl. No.: 14/448,406

(22) Filed: Jul. 31, 2014

(65) Prior Publication Data

US 2014/0343423 A1    Nov. 20, 2014

Related U.S. Application Data

(63) Continuation of application No. PCT/JP2012/077441, filed on Oct. 24, 2012.

(30) Foreign Application Priority Data

Feb. 20, 2012   (JP) ................. 2012-033828

(51) Int. Cl.
*A61B 8/00*   (2006.01)
*A61B 8/08*   (2006.01)
(Continued)

(52) U.S. Cl.
CPC .............. *A61B 8/0891* (2013.01); *A61B 8/02* (2013.01); *A61B 8/5207* (2013.01);
(Continued)

(58) Field of Classification Search
CPC ....... A61B 8/0891; A61B 8/5207; A61B 8/02; A61B 8/5223; A61B 8/486; A61B 5/02007; A61B 8/485
See application file for complete search history.

(56) References Cited

U.S. PATENT DOCUMENTS 5,840,028 A    11/1998   Chubachi et al.
2003/0191399 A1*  10/2003  Muramatsu ........ A61B 5/02241
                                                        600/480
(Continued)

FOREIGN PATENT DOCUMENTS

CN    1917818 A    2/2007
JP    2004-290408 A    10/2004
JP    3652791 B2    5/2005

OTHER PUBLICATIONS

Extended European Search Report, dated Sep. 24, 2015, for European Application No. 12869293.6

(Continued)

*Primary Examiner* — Jonathan Cwern
(74) *Attorney, Agent, or Firm* — Birch, Stewart, Kolasch & Birch, LLP

(57) ABSTRACT

In an ultrasound diagnostic apparatus, a vascular wall tracker tracks pulsation-originated vascular wall movement based on reception signals obtained through transmission and reception of ultrasonic beams by an ultrasound probe to and from a subject, and a pulsating timing determiner determines pulsating timing by detecting pulsation-originated periodic changes in the vascular wall movement tracked by the vascular wall tracker in each of sound rays, obtaining a detection time point as a pulsating timing candidate in each of the sound rays, and statistically analyzing pulsating timing candidates in the respective sound rays within a single pulse duration. The ultrasound diagnostic apparatus can accurately measure the state of a blood vessel merely using information obtained through ultrasound examination without electrocardiographic waveforms.

18 Claims, 3 Drawing Sheets

(51) Int. Cl.
*A61B 8/02* (2006.01)
*A61B 5/02* (2006.01)
(52) U.S. Cl.
CPC ........ *A61B 8/5223* (2013.01); *A61B 5/02007* (2013.01); *A61B 8/485* (2013.01); *A61B 8/486* (2013.01)

(56) References Cited

U.S. PATENT DOCUMENTS

2008/0021318 A1    1/2008  Kato et al.
2010/0331715 A1*  12/2010  Addison ............ A61B 5/02028
                                                                        600/529

OTHER PUBLICATIONS

International Search Report, dated Jan. 15, 2013, issued in PCT/JP2012/077441.
Chinese Office Action and Search Report, dated Aug. 4, 2015, for Chinese Application No. 201280070093.4 with an English translation of the Office Action.
Forms PCT/IB/338, PCT/IB/373 and PCT/ISA/237, dated Sep. 4, 2014, for International Application No. PCT/JP2012/077441.

* cited by examiner

ULTRASOUND DIAGNOSIS DEVICE AND ULTRASOUND IMAGE GENERATION METHOD

CROSS-REFERENCE TO RELATED APPLICATIONS

This application is a Continuation of PCT International Application No. PCT/JP2012/077441 filed on Oct. 24, 2012, which claims priority under 35 U.S.C. § 119(a) to Japanese Application No. 2012-033828 filed on Feb. 20, 2012. The above application(s) is hereby expressly incorporated by reference, in its entirety, into the present application.

BACKGROUND OF THE INVENTION

The present invention relates to an ultrasound diagnostic apparatus and a method for producing an ultrasound image, and particularly to an ultrasound diagnostic apparatus and a method for producing an ultrasound image of a vascular wall.

Conventionally, ultrasound diagnostic apparatuses using ultrasound images have been employed in the medical field. In general, this type of ultrasound diagnostic apparatus comprises an ultrasound probe having a built-in transducer array and an apparatus body connected to the ultrasound probe. The ultrasound probe transmits ultrasonic waves toward a subject, receives ultrasonic echoes from the subject, and the apparatus body electrically processes the reception signals to produce an ultrasound image.

In addition, such an ultrasound diagnostic apparatus may acquire various kinds of information indicative of the condition of a disease based on reception signals obtained by receiving ultrasonic echoes from the subject. For example, ultrasonic waves are transmitted to and received from a blood vessel, and the resulting reception signals are used to acquire information such as elastic characteristics of a vascular wall, a thickness of the vascular wall and a thickness of the vascular diameter in circulatory diseases including arteriosclerosis and cerebral infarction. Values included in such information vary with the progression of arteriosclerosis, so that the condition of a circulatory disease can be estimated by observing the values.

However, since the thickness of a vascular wall is small and also is affected by pulsation due to cardiac beats, the information on the blood vessels as described above contains a significant amount of noise components. Accordingly, there is a demand for an ultrasound diagnostic apparatus capable of measuring the state of a blood vessel while suppressing the noise components.

As a technology for accurately measuring the state of a blood vessel, an ultrasound diagnostic apparatus that tracks a position of a vascular wall based on a reception signal to identify positions of a front wall and a rear wall of a blood vessel, based on which a change-waveform of a blood vessel is generated, thereby measuring changes in the vascular diameter over time has been proposed, as disclosed by JP 2004-290408 A.

The ultrasound diagnostic apparatus presented by JP 2004-290408 A can accurately measure the state of a blood vessel by identifying pulsating timing using electrocardiographic waveforms and, based on the pulsating timing, removing noise components associated with cardiac beats from a change-waveform of a blood vessel. However, there was a problem that, due to the necessity of obtaining electrocardiographic waveforms in addition to ultrasound information, the apparatus would increase in size to thus impair its mobility, resulting in poor applicability for diagnosis in various places.

SUMMARY OF THE INVENTION

The present invention has been made to solve the above-described problem of the prior art and has an object to provide an ultrasound diagnostic apparatus and a method for producing an ultrasound image that can accurately measure the state of a blood vessel merely using information obtained through ultrasound examination without electrocardiographic waveforms.

The ultrasound diagnostic apparatus for transmitting and receiving ultrasonic beams by an ultrasound probe to and from a subject and producing an ultrasound image based on reception signals outputted from the ultrasound probe according to the present invention comprises: a vascular wall tracker configured to track pulsation-originated vascular wall movement based on the reception signals obtained through transmission and reception of ultrasonic beams between a blood vessel of the subject and the ultrasound probe; and a pulsating timing determiner configured to determine pulsating timing by detecting pulsation-originated periodic changes in the vascular wall movement tracked by the vascular wall tracker in each of sound rays, obtaining a detection time point as a pulsating timing candidate in each of the sound rays, and statistically analyzing pulsating timing candidates in the respective sound rays within a single pulse duration.

Preferably, the pulsating timing determiner obtains at least one of a velocity waveform of diameter-change of a vascular wall and a diameter-change waveform of the vascular wall based on the vascular wall movement tracked by the vascular wall tracker and detects a maximum value or a minimum value periodically appearing in the obtained at least one waveform for every sound ray to thereby detect periodic changes of the vascular wall.

The pulsating timing determiner can calculate an average value or a median of pulsating timing candidates in the respective sound rays within a single pulse duration to thereby determine the pulsating timing. The pulsating timing determiner can calculate the average value or the median during a period of 0.05 second including the detection time point to thereby obtain the pulsating timing candidate.

The pulsating timing determiner can obtain a degree as a number of, among all of the sound rays, sound rays in which periodic vascular wall movement is detected in every pulse duration, and exclude a pulse duration in which the degree as the number of sound rays does not exceed a predetermined value from determination of the pulsating timing. The pulsating timing determiner can obtain the degree as the number of sound rays with which periodic vascular wall movement is detected in a period of 0.05 second including the detection time point and exclude a pulse duration in which the degree as the number of sound rays does not exceed a predetermined value from determination of the pulsating timing.

The pulsating timing determiner can obtain a velocity waveform of diameter-change of a vascular wall based on the vascular wall movement tracked by the vascular wall tracker and exclude a pulse duration in which a maximum value periodically appearing in the obtained waveform does not exceed a predetermined value from determination of the pulsating timing.

It is preferable that the ultrasound diagnostic apparatus further comprises a vascular wall elastic characteristics calculator configured to calculate elastic characteristics of a vascular wall based on the pulsating timing determined by the pulsating timing determiner. It is also preferable that the ultrasound diagnostic apparatus further comprises a thickness calculator configured to calculate at least one of a thickness of a vascular wall and a thickness of a vascular diameter based on the pulsating timing determined by the pulsating timing determiner.

The method for producing an ultrasound image by transmitting and receiving ultrasonic beams by an ultrasound probe to and from a subject and producing an ultrasound image based on reception signals outputted from the ultrasound probe according to the present invention comprises: tracking pulsation-originated vascular wall movement based on the reception signals obtained through transmission and reception of the ultrasonic beams between a blood vessel of the subject and the ultrasound probe; and determining pulsating timing by detecting pulsation-originated periodic changes in the tracked vascular wall movement in each of sound rays, obtaining a detection time point as a pulsating timing candidate in each of the sound rays, and statistically analyzing pulsating timing candidates in the respective sound rays within a single pulse duration.

According to the present invention, a periodic change of a vascular wall is detected in every sound ray to obtain a detection time point as a pulsating timing candidate for each of the sound rays, and the pulsating timing candidates of the respective sound rays are statistically analyzed within a single pulse duration, thereby determining pulsating timing. Accordingly, the state of a blood vessel can be accurately measured by not using electrocardiographic waveforms but merely using information obtained through ultrasound examination.

DETAILED DESCRIPTION OF THE INVENTION

The embodiment of the present invention will be described below based on the appended drawings.

Figure 1:
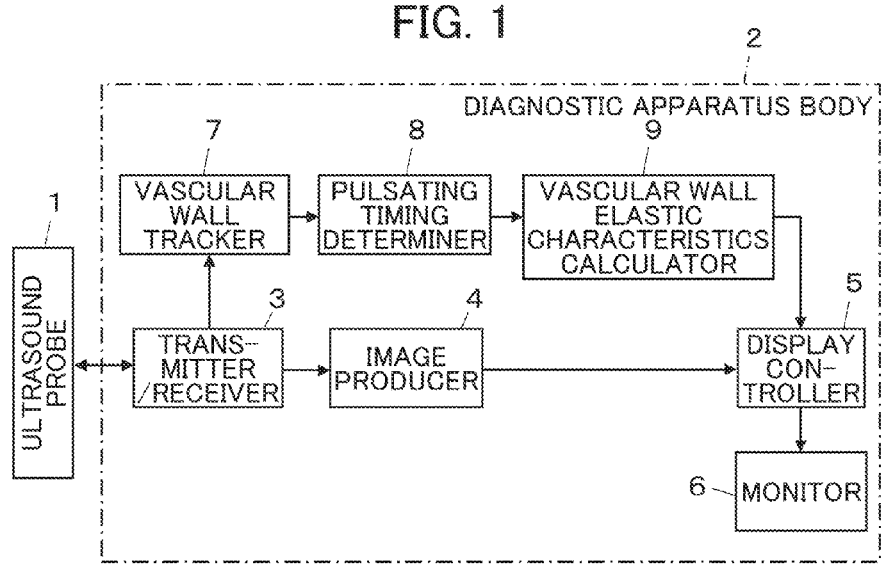
FIG. 1 is a block diagram showing a configuration of an ultrasound diagnostic apparatus according to an embodiment of the present invention.

FIG. 1 shows a configuration of an ultrasound diagnostic apparatus according to the embodiment. The ultrasound diagnostic apparatus comprises an ultrasound probe 1 for transmission and reception of ultrasonic waves and a diagnostic apparatus body 2 connected to the ultrasound probe 1. The diagnostic apparatus body 2 produces image data representing an ultrasound image based on reception signals acquired through transmission and reception of ultrasonic waves by the ultrasound probe 1 and also determines pulsating timing based on pulsation-originated vascular wall movement to calculate elastic characteristics of a vascular wall.

The ultrasound probe 1 is a probe of, for example, convex type, linear scan type, or sector scan type, which is brought into contact with a body surface of a subject when used. The ultrasound probe 1 comprises a plurality of ultrasound transducers arranged one-dimensionally or two-dimensionally. The ultrasound transducers transmit ultrasonic waves toward a subject based on applied actuation signals and receives ultrasonic echoes bounced off the subject to output reception signals.

Each of the ultrasound transducers is composed of a vibrator including a piezoelectric body made of, for example, a piezoelectric ceramic typified by Pb (lead) zirconate titanate (PZT) or a piezoelectric polymer typified by polyvinylidene difluoride (PVDF) and electrodes provided on both ends of the piezoelectric body. Application of a pulsed or continuous-wave voltage to electrodes of the vibrators causes the piezoelectric bodies to expand and contract. The expansion and contraction cause the vibrators to produce pulsed or continuous-wave ultrasonic waves, which are combined to form an ultrasonic beam. Upon reception of propagating ultrasonic waves, the vibrators expand and contract to produce electric signals. The electric signals are outputted as reception signals of ultrasonic waves.

The diagnostic apparatus body 2 comprises a transmitter/receiver 3 connected to the ultrasound probe 1. The transmitter/receiver 3 is connected to an image producer 4, which in turn is connected through a display controller 5 to a monitor 6. The transmitter/receiver 3 is also connected to a vascular wall tracker 7, a pulsating timing determiner 8, and a vascular wall elastic characteristics calculator 9 in order. The vascular wall elastic characteristics calculator 9 is connected to the display controller 5.

The transmitter/receiver 3 incorporates a transmission circuit and a reception circuit. The transmission circuit comprises a plurality of channels and produces a plurality of actuation signals applied to the respective ultrasound transducers of the ultrasound probe 1. In that process, the actuation signals can be given respective delays based on a predetermined transmission delay pattern. The transmission circuit adjusts delay amounts of the actuation signals so as to allow ultrasonic waves transmitted from the ultrasound transducers to form an ultrasonic beam and supplies the adjusted actuation signals to the ultrasound probe 1.

The reception circuit of the transmitter/receiver 3 comprises a plurality of channels to receive and amplify a plurality of analog reception signals outputted from the respective ultrasound transducers and converts the signals into digital reception signals. The reception circuit also provides each of the reception signals with a delay corresponding to a focus position based on a predetermined reception delay pattern, and adds up the reception signals for each focus position to perform reception focusing processing. By this reception focusing processing, a plurality of sound ray signals (sound ray data) in which the focal points of the ultrasonic echoes are made to converge are generated.

Next, the sound ray data undergo envelope detection processing by means of, for example, low-pass filter processing, followed by attenuation correction according to the distance depending on a depth of the ultrasonic wave reflection position using STC (Sensitivity Time gain Control).

The sound ray data thus processed are sequentially stored in a data memory having a sufficient memory capacity for accumulating sound ray data for a plurality of frames. Having an image data producing function, the reception circuit is inputted with sound ray data directly supplied in a live mode and sound ray data supplied from the data memory in a freeze mode, and performs pre-processing such as Log (logarithmic) compression and gain adjustment on the sound ray data to produce image data, which are outputted to the image producer 4.

The image producer 4 converts the image data of an ultrasound image supplied from the reception circuit of the transmitter/receiver 3 into image data compatible with the ordinary television signal scanning method through raster conversion and performs necessary image processing such as gradation processing before supplying the data to the display controller 5.

The display controller 5 causes the monitor 6 to display an ultrasound diagnostic image based on the image data supplied from the image producer 4. The monitor 6 includes a display device such as an LCD, for example, and displays an ultrasound diagnostic image under the control of the display controller 5.

The vascular wall tracker 7 is capable of tracking vascular wall movement based on the sound ray data supplied from the reception circuit of the transmitter/receiver 3. The phase difference tracking technique described in JP 3652791 B, for example, can be adopted for the tracking process, in which amplitude information and phase information of the sound ray data inputted from the transmitter/receiver 3 are calculated, and by using the calculated information, pulsation-originated vascular wall movement is accurately tracked. Information on the vascular wall movement obtained through the tracking process is outputted to a pulsating timing determiner 8.

The pulsating timing determiner 8 detects pulsation-originated periodic changes of a vascular wall for every sound ray based on the information on the vascular wall movement supplied from the vascular wall tracker 7 and also finds a detection time point as a pulsating timing candidate in each of the sound rays. Thereafter, the pulsating timing determiner 8 statistically analyzes the pulsating timing candidates of the respective sound rays within a single pulse duration to thereby determine the pulsating timing.

A vascular wall elastic characteristics calculator 9 calculates the elastic characteristics of a vascular wall based on the vascular wall movement tracked by the vascular wall tracker 7 and on the pulsating timing determined by the pulsating timing determiner 8 and causes the monitor 6 to display the calculated elastic characteristics of the vascular wall through the display controller 5.

Next, the operation of this embodiment will be described.

Figure 2:
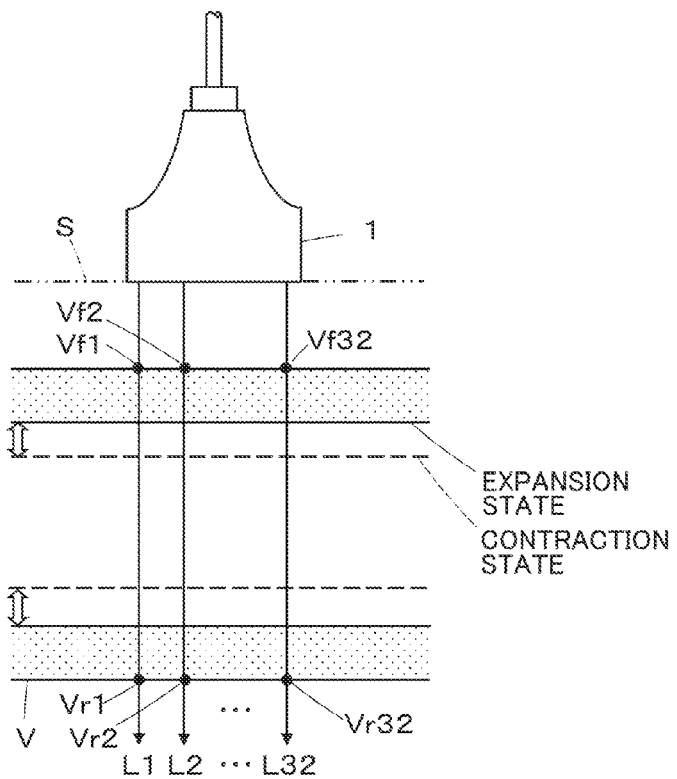
FIG. 2 is a diagram showing sound rays produced by transmission and reception of ultrasonic beams to and from a vascular wall.

First, as illustrated in FIG. 2, upon being placed in contact with a body surface of a subject S, the ultrasound probe 1 transmits ultrasonic beams toward a blood vessel in the subject S in response to actuation signals from the transmission circuit of the transmitter/receiver 3 of the diagnostic apparatus body 2. FIG. 2 illustrates the ultrasound probe 1 as being placed on the body surface of the subject S such that ultrasonic beams enter in the direction perpendicular to the longitudinal direction of a vascular wall V. The ultrasonic beams that have entered into the vascular wall V are bounced off various parts such as a front wall Vf and a rear wall Vr of the vascular wall V, and the resulting ultrasonic echoes are received by the respective ultrasound transducers of the ultrasound probe 1. At this time, the vascular wall V periodically moves so as to repeat expansion and contraction in response to pulsation, and the ultrasonic beams are continuously transmitted and received during at least one cycle of periodic change of the vascular wall V.

Upon receiving the ultrasonic echo, each of the ultrasound transducers outputs a reception signal according to the intensity of the received ultrasonic echo to the reception circuit of the transmitter/receiver 3. Based on the outputted reception signal, sound ray digital data are produced by the reception circuit for each frame, and in addition, based on the intensity (magnitude of amplitude) of the sound ray signals, image data are produced for each frame. In an example, B-mode tomographic image data can be produced by displaying intensities of sound ray signals as luminance, and M-mode image data can be further produced by displaying changes in the B-mode tomographic image over time. The image data of the vascular wall V thus produced are outputted from the transmitter/receiver 3 to the image producer 4. In the meantime, the sound ray data of each frame are outputted from the transmitter/receiver 3 to the vascular wall tracker 7.

The image data inputted to the image producer 4 are subjected to necessary image processing such as gradation processing and are then outputted to the display controller 5, so that an ultrasound image such as a B-mode tomographic image or an M-mode image is displayed on the monitor 6.

The vascular wall tracker 7, on the other hand, tracks pulsation-originated movement of the vascular wall V by detecting the position of the vascular wall V in each frame based on amplitude information and phase information of the sound ray data inputted from the transmitter/receiver 3. More specifically, upon comparing sound ray data among frames, those data having changes not in amplitudes (intensities) but only in phases (positions in the respective frames) are regarded as representing changes in movement of a single object, whereby movement of the vascular wall V is tracked.

The tracked movement of the vascular wall V is outputted from the vascular wall tracker 7 to the pulsating timing determiner 8, and based on the movement of the vascular wall V, the pulsating timing determiner 8 determines the periodic pulsating timing associated with pulsation. In this process, pulsation-originated periodic movement of the vascular wall V is detected in, for example, each of 32 sound rays L1 to L32, to thereby obtain the pulsating timing.

Figure 3:
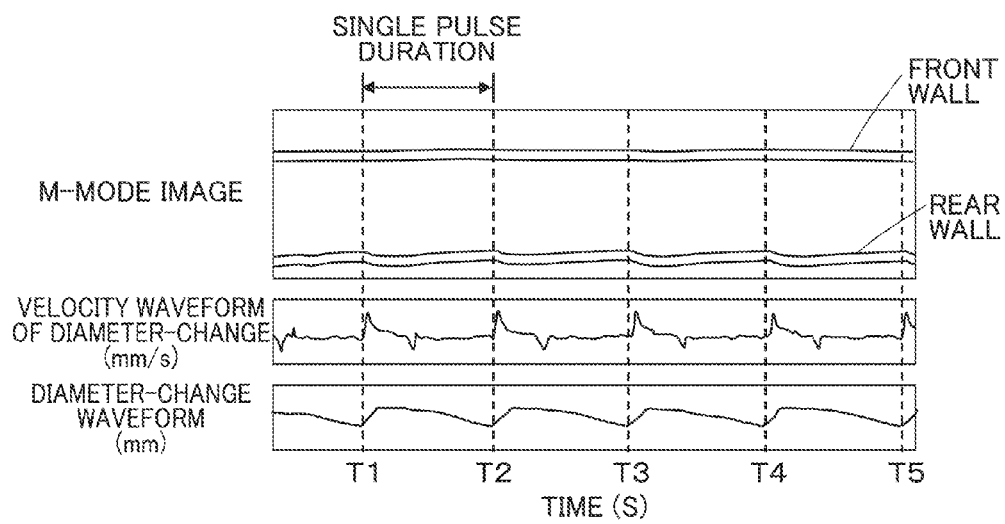
FIG. 3 is a diagram showing a velocity waveform of diameter changes and a diameter-change waveform obtained for each of sound rays.

Specifically, in order to detect periodic movement of a particular site of the vascular wall V, e.g., an outside diameter of the vascular wall V, positional (phase) differences between a front wall Vf1 and a rear wall Vr1, between a front wall Vf2 and a rear wall Vr2, . . . and between a front wall Vf32 and a rear wall Vr 32 respectively positioned on the sound rays L1 to L32 are taken, and the outside diameter of the vascular wall V is calculated for each of the sound rays L1 to L32 in each frame, thereby obtaining a velocity waveform of diameter-change and a diameter-change waveform of the vascular wall V. FIG. 3 illustrates an example of velocity waveforms of diameter-change and a diameter-change waveforms obtained in the respective sound rays L1 to L32. FIG. 3 reveals that the velocity waveform of diameter-change and the diameter-change waveform also have similar periodic changes to the periodic movement of the vascular wall V appearing in the M-mode image. Accordingly, pulsation-originated periodic change of the vascular wall V can be detected by, for example, detecting the minimum value which periodically appears in the diameter-change waveform, that is, detecting time points T1 to T5 at which the vascular diameter periodically becomes smallest in each of the sound rays L1 to L32. Thereafter, the detection time points T1 to T5 are obtained respectively as pulsating timing candidates of the first to fifths pulses in each of the sound rays L1 to L32. The periodic change of the vascular wall V is not particularly limited to that found through detection of the minimum value in the diameter-change waveform but may be anything representing periodic change of the vascular wall V such as the maximum value periodically appearing in the velocity waveform of diameter-change.

Table 1 shows the detection time points (pulsating timing candidates) at which the minimum value in the diameter-change waveform indicative of the first to fifth pulses is detected in each of the sound rays L1 to L32. The pulsating timing candidates are each expressed as an elapsed time since the start of detection and are arranged by pulse durations in order of the sound rays L1 to L32 in the table. Pulsating timing candidates detected in the respective sound rays L1 to L32 in the same pulse duration were supposed to be the same time point. However, in the first pulse, the pulsating timing candidate in the sound ray L4 was detected at 0.15 second, while the pulsating timing candidate in the sound ray L5 was detected at 0.20 second, for example. This is because noises associated with cardiac beats varied the time points of the pulsating timing candidates detected in the respective sound rays L1 to L32. Meanwhile, the symbol "-" shown in the cells of, for example, the first and second pulses of the sound ray L2 teaches that no pulsating timing candidate was detected because of noise influence.

TABLE 1

Table 1

| sound ray | 1st pulse | 2nd pulse | 3rd pulse | 4th pulse | 5th pulse |
|---|---|---|---|---|---|
| | | | in seconds | | |
| L1 | — | — | 1.625 | — | — |
| L2 | — | — | 1.625 | 2.385 | 3.17 |
| L3 | 0.15 | — | 1.625 | 2.375 | 3.165 |
| L4 | 0.15 | — | 1.625 | 2.375 | 3.165 |
| L5 | 0.2 | 0.9 | 1.625 | 2.375 | — |
| . | . | . | . | . | . |
| . | . | . | . | . | . |
| . | . | . | . | . | . |
| L28 | 0.21 | 0.905 | 1.625 | 2.385 | 3.165 |
| L29 | — | 0.905 | 1.625 | 2.385 | 3.165 |
| L30 | — | 0.905 | 1.625 | 2.385 | 3.165 |
| L31 | 0.2 | 0.905 | 1.625 | 2.385 | 3.165 |
| L32 | 0.2 | 0.905 | 1.625 | 2.38 | 3.165 |
| average value | 0.19 | 0.904 | 1.625 | 2.383 | 3.165 |
| median | 0.2 | 0.905 | 1.625 | 2.385 | 3.165 |
| degree as number of sound rays | 27 | 20 | 30 | 29 | 29 |

Therefore, in order to prevent variation in the pulsating timing candidates from affecting determination of the pulsating timing, the pulsating timing candidates in the respective sound rays L1 to L32 are statistically processed within the same pulse duration to determine the pulsating timing.

As an example, as shown in Table 1, the pulsating timing determiner 8 calculates the average value or median of the pulsating timing candidates in the respective sound rays L1 to L32 in the same pulse duration, and accordingly one pulsating timing can be determined for each pulse. Since occurrence of the above-described variation in the pulsating timing candidates becomes higher in the sound rays closer to both ends (sound rays L1 and L32) among the sound rays L1 to L32, the average value is preferably calculated using the pulsating timing candidates detected in sound rays in the central portion among the sound rays L1 to L32, excluding several sound rays near the both ends. The maximum value which periodically appears in the velocity waveform of diameter-change illustrated in FIG. 3 is compared to one another among all of the sound rays L1 to L32, and the pulsating timing candidate in the sound ray where the maximum value is equal to or lower than a predetermined value is judged as containing a large amount of noise component, i.e., less reliable as a pulsating timing candidate, thereby being excluded from determination of the pulsating timing.

Figure 4:
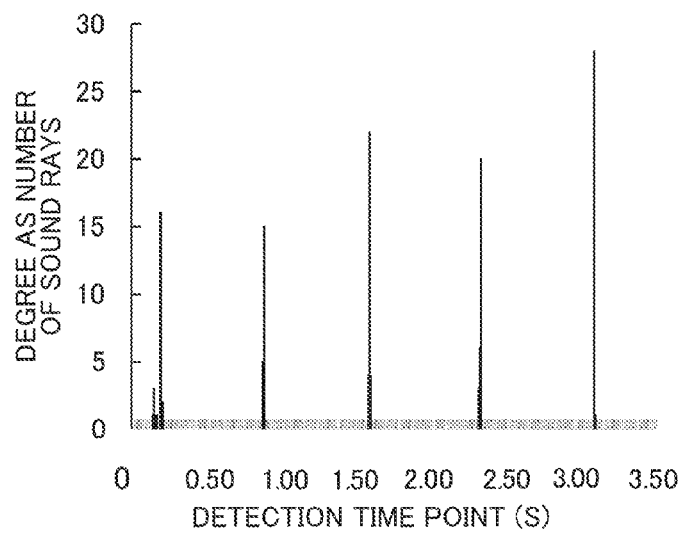
FIG. 4 is a graph showing degrees as numbers of sound rays in which periodic changes of a vascular wall have been detected.

The pulsating timing determiner 8 can also statistically evaluate reliability of each of the pulsating timings which have been determined for multiple pulse durations, and exclude a pulse duration whose reliability is low from determination of pulsating timing. For instance, reliability can be evaluated based on variations in the pulsating timing candidates among the respective pulse durations. FIG. 4 illustrates a histogram showing degrees as numbers of the sound rays L1 to L32 shown in Table 1 at the detection time points. Looking at the degree of the first pulse as an example, Table 1 shows that the pulsating timing candidates were detected in 27 sound rays out of the sound rays L1 to L32 (the pulsating timing candidates were not detected in the other sound rays, for which the symbol "-" is shown), while FIG. 4 shows that among the 27 sound rays in which the pulsating timing candidates were detected, the pulsating timing candidates were detected at the same time point of 0.2 S in 16 sound rays. FIG. 4 illustrates the degrees as numbers of sound rays which showed the same detection time point among the sound rays L1 to L32 at each of the detection time points. In FIG. 4, the pulse duration in which the degree as the number of, among the sound rays L1 to L32, sound rays having the same detection time point is equal to or lower than the predetermined value, e.g., the pulse duration in which the degree as the number of, among the sound rays L1 to L32, sound rays having the same detection time point is 50% or lower or 80% or lower can be judged as less reliable due to a large variation in the pulsating timings, that is, as the pulse duration containing a large amount of noise component, and thus can be excluded from determination of the pulsating timing. In addition, the maximum values in the velocity waveform of diameter-change obtained in the respective sound rays L1 to L32 are averaged in each of the pulse durations, and the obtained average values are compared among the multiple pulse durations, whereby the pulse duration having the average value equal to or lower than the predetermined value can be judged as less reliable and can be excluded from determination of the pulsating timing.

In this manner, the pulsating timing can be accurately obtained by statistically processing the pulsating timing candidates and determining the pulsating timing. Further, the pulsating timing can be obtained even with the higher accuracy by subjecting the determined pulsating timing to statistical processing and evaluating reliability thereof.

The determined pulsating timing is outputted from the pulsating timing determiner 8 to the vascular wall elastic characteristics calculator 9, where the elastic characteristics of the vascular wall is calculated based on the pulsating timing. For example, based on the pulsating timing, an end stage of a diastole in which the vascular wall V becomes thickest within one cardiac beat and a systole in which the vascular wall V becomes thinnest within one cardiac beat are obtained, and in addition, a thickness ($h_{di}$) of the vascular wall V at an end stage of a diastole and the maximum value ($\Delta h_t$) of thickness variation of the vascular wall V during a systole are both obtained, whereby a strain amount $\varepsilon_i$ in the direction of the vascular wall diameter is calculated as the elastic characteristics of the vascular wall V in accordance with the following formula (1).

$$\varepsilon_i = \Delta h_i / h_{di} \tag{1}$$

The calculated elastic characteristics of the vascular wall V is outputted from the vascular wall elastic characteristics calculator 9 and displayed on the monitor 6 via the display controller 5.

According to this embodiment, following removal of noises associated with cardiac beats, the pulsating timing is precisely determined. Hence, the elastic characteristics of the vascular wall V can be accurately calculated by not using electrocardiographic waveforms but using only information obtained through ultrasound examination.

In the above-described embodiment, a single pulsating timing candidate is obtained in each of the sound rays L1 to L32 based on one detection time point at which the minimum value in the diameter-change waveform was detected in every pulse duration. However, a certain period of time including the detection time point at which the minimum value was detected can be statistically processed to thereby obtain a single pulsating timing candidate in each of the sound rays L1 to L32. As an example, a range of 0.05 S in which variation in the diameter-change waveform due to noises stabilizes is grouped to be a certain period of time. The pulsating timing determiner 8 calculates, in each of the sound rays L1 to L32 in every pulse duration, an average value or median of detection time points of sound rays whose detection time points at which the minimum value in the diameter-change waveform is detected are included in the certain period of time of 0.05 S, to thereby statistically obtain a single pulsating timing candidate in each of the sound rays L1 to L32. The respective pulsating timing candidates thus obtained are then statistically processed, whereby a single pulsating timing can be determined. The pulsating timing determiner 8 can also obtain, in each of the sound rays L1 to L32 in every pulse duration, a degree as the number of sound rays whose detection time points at which the minimum value in the diameter-change waveform is detected are included in the certain period of time of 0.05 S, to thereby judge a pulse duration having the degree equal to or lower than the predetermined value as less reliable and exclude the pulse duration from determination of pulsating timing.

Figure 5:
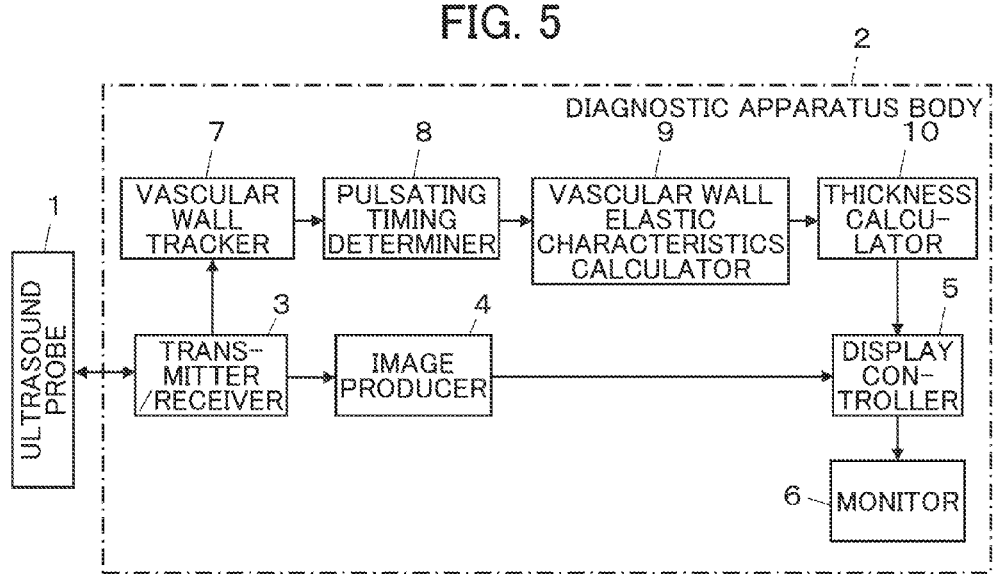
FIG. 5 is a block diagram showing a configuration of an ultrasound diagnostic apparatus according to a modification example.

As illustrated in FIG. 5, a thickness calculator 10 can be additionally provided between the vascular wall elastic characteristics calculator 9 and the display controller 5. The thickness calculator 10 can precisely calculate a thickness of the vascular wall V and a diameter size of the vascular wall V based on the pulsating timing determined by the pulsating timing determiner 8. The thickness of the vascular wall V and the diameter size of the vascular wall V vary depending on progression of arteriosclerosis. By obtaining these values precisely without using electrocardiographic waveforms, the condition of a circulatory disease can be accurately estimated by using only information obtained through ultrasound examination.

In the embodiment described above, movement of the vascular wall V is tracked by the vascular wall tracker 7 based on the sound ray data supplied from the transmitter/receiver 3, but this is not the sole case, and the data supplied to the vascular wall tracker 7 only require to contain the information used to track movement of the vascular wall V. For example, the transmitter/receiver 3 can supply the vascular wall tracker 7 with image data, and the vascular wall tracker 7 can track movement of the vascular wall V based on luminance information or the like contained in the image data supplied by the transmitter/receiver 3.

Moreover, in the embodiment described above, periodic movement of the outside diameter of the vascular wall V is detected by the vascular wall tracker 7 to obtain the pulsating timing candidates, but the invention is not limited to this embodiment, as long as periodic movement of any part of the vascular wall V can be obtained. For example, the pulsating timing candidates can be obtained by detecting periodic movement of the front wall Vf or of the rear wall Vr of the vascular wall V.

What is claimed is:

1. A method for producing an ultrasound image comprising:
    transmitting ultrasonic beams from an ultrasound probe having a plurality of ultrasound transducers to a subject;
    performing reception focusing processing by using reception signals outputted from the plurality of ultrasound transducers in the ultrasound probe which have received ultrasonic echoes from the subject to obtain sound ray signals corresponding to sound rays;
    producing an ultrasound image based on the sound ray signals;
    tracking a vascular wall movement in each of the sound rays due to cardiac beats of the subject based on the sound ray signals;
    obtaining a diameter-change waveform representing a temporal transition in an outer diameter of a vascular wall based on the tracked vascular wall movement in each of the sound rays;
    detecting a minimum value periodically appearing in the obtained diameter-change waveform in each of the sound rays;
    obtaining a detection time point at which the minimum value is detected as a pulsating timing candidate of the subject in each of the sound rays; and
    statistically analyzing obtained pulsating timing candidates in the sound rays within a single pulse duration in cardiac beats of the subject to determine a pulsating timing in cardiac beats of the subjects without using electrocardiographic waveforms.

2. The method for producing an ultrasound image according to claim 1, wherein the pulsating timing is determined by calculating an average value or a median of pulsating timing candidates for the sound rays within the single pulse duration.

3. The method for producing an ultrasound image according to claim 2, wherein the pulsating timing is determined by calculating the average value or the median of pulsating timing candidates for the sound rays whose detection time points are included within a period of 0.05 seconds.

4. The method for producing an ultrasound image according to claim 1, wherein a number of, among all of the sound rays, sound rays in which the minimum value is detected is obtained in every pulse duration, and the pulsating timing is determined only for the pulse duration in which the obtained number of sound rays exceeds a predetermined value.

5. The method for producing an ultrasound image according to claim 4, wherein the number of sound rays whose detection time points are included within a period of 0.05 seconds is obtained.

6. The method for producing an ultrasound image according to claim 1, wherein a velocity waveform of diameter-change representing a temporal transition in change velocity of the outer diameter of the vascular wall based on the tracked vascular wall movement is obtained, and the pulsating timing only for the single pulse duration in which the maximum value periodically appearing in the obtained velocity waveform of diameter-change exceeds a predetermined value is determined.

7. The method for producing an ultrasound image according to claim 1, wherein after determining the pulsating timing, characteristics of the vascular wall are calculated based on the pulsating timing.

8. The method for producing an ultrasound image according to claim 1, wherein after determining the pulsating timing, at least one of a thickness of the vascular wall and a vascular diameter is calculated based on the pulsating timing.

9. The method for producing an ultrasound image according to claim 1, wherein the pulsating timing is determined using only information obtained via ultrasound examination.

10. A method for producing an ultrasound image comprising:
    transmitting ultrasonic beams from an ultrasound probe having a plurality of ultrasound transducers to a subject;
    performing reception focusing processing by using reception signals outputted from the plurality of ultrasound transducers in the ultrasound probe which have received ultrasonic echoes from the subject to obtain sound ray signals corresponding to sound rays;
    producing an ultrasound image based on the sound ray signals;
    tracking a vascular wall movement in each of the sound rays due to cardiac beats of the subject based on the sound ray signals;
    obtaining a velocity waveform of diameter-change representing a temporal transition in change velocity of an outer diameter of a vascular wall based on the tracked vascular wall movement in each of the sound rays;
    detecting a maximum value periodically appearing in the obtained velocity waveform of diameter-change in each of the sound rays;
    obtaining a detection time point at which the maximum value is detected as a pulsating timing candidate of the subject in each of the sound rays; and
    statistically analyzing obtained pulsating timing candidates in the sound rays within a single pulse duration in cardiac beats of the subject to determine a pulsating timing in cardiac beats of the subject without using electrocardiographic waveforms.

11. The method for producing an ultrasound image according to claim 10, wherein the pulsating timing is determined by calculating an average value or a median of pulsating timing candidates for the sound rays within the single pulse duration.

12. The method for producing an ultrasound image according to claim 10, wherein the pulsating timing is determined by calculating the average value or the median of the pulsating timing candidates for the sound rays whose detection time points are included within a period of 0.05 seconds.

13. The method for producing an ultrasound image according to claim 10, wherein a number of, among all of the sound rays, sound rays in which the maximum value is detected is obtained in every pulse duration, and the pulsating timing is determined only for the pulse duration in which the obtained number of sound rays exceeds a predetermined value.

14. The method for producing an ultrasound image according to claim 13, wherein the number of sound rays whose detection time points are included within a period of 0.05 seconds is obtained.

15. The method for producing an ultrasound image according to claim 10, wherein the pulsating timing only for the single pulse duration in which the maximum value periodically appearing in the obtained velocity waveform of diameter-change exceeds a predetermined value is determined.

16. The method for producing an ultrasound image according to claim 10, wherein after determining the pulsating timing, characteristics of the vascular wall are calculated based on the pulsating timing.

17. The method for producing an ultrasound image according to claim 10, wherein after determining the pulsating timing, at least one of a thickness of the vascular wall and a vascular diameter is calculated based on the pulsating timing.

18. The method for producing an ultrasound image according to claim 10, wherein the pulsating timing is determined using only information obtained via ultrasound examination.

* * * * *